US012576182B2

(12) United States Patent
Veruva et al.

(10) Patent No.: US 12,576,182 B2
(45) Date of Patent: Mar. 17, 2026

(54) ABSORBABLE DRESSINGS FOR SEALING SENSITIVE NEURAL TISSUE AND DURA MATTER

(71) Applicant: Ethicon, Inc., Raritan, NJ (US)

(72) Inventors: Sai Veruva, Somerville, NJ (US); Leo B. Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 298 days.

(21) Appl. No.: 18/448,226

(22) Filed: Aug. 11, 2023

(65) Prior Publication Data

US 2025/0049984 A1 Feb. 13, 2025

(51) Int. Cl.
*A61L 24/00* (2006.01)
*A61L 24/04* (2006.01)

(52) U.S. Cl.
CPC ......... *A61L 24/0042* (2013.01); *A61L 24/043* (2013.01); *A61L 2300/442* (2013.01); *A61L 2400/04* (2013.01); *A61L 2420/02* (2013.01)

(58) Field of Classification Search
CPC ............. A61L 24/0042; A61L 24/0046; A61L 24/0047; A61L 24/043; A61L 24/10; A61L 2300/442; A61L 2400/00; A61L 2400/04; A61L 2420/00; A61L 2420/02; A61F 13/00; A61F 13/00055; A61F 13/00059; A61F 13/00072; A61F 13/00076; A61F 13/0246; A61F 13/025; A61F 13/0253; A61F 13/0256; A61F 13/0276; A61F 13/0283; A61F 13/0286; A61F 13/0289; A61F 2013/00217; C09J 7/30; C09J 7/32; C09J 2301/408; C09J 2301/502
See application file for complete search history.

(56) References Cited

U.S. PATENT DOCUMENTS

| | | | | | |
|---|---|---|---|---|---|
| 5,653,224 | A | * | 8/1997 | Johnson | ................ A61F 13/023 |
| | | | | | 602/41 |
| 7,396,976 | B2 | | 7/2008 | Hurwitz et al. | |
| 8,381,498 | B2 | | 2/2013 | Epstein | |
| 8,852,230 | B2 | | 10/2014 | Sawhney et al. | |
| 8,932,619 | B2 | | 1/2015 | Ladet et al. | |
| 8,957,277 | B2 | | 2/2015 | Carty et al. | |
| 9,416,228 | B2 | | 8/2016 | Bender et al. | |
| 9,926,470 | B2 | | 3/2018 | Carty | |
| 9,956,311 | B2 | | 5/2018 | Ericson | |
| 10,155,062 | B2 | | 12/2018 | Dalal et al. | |

(Continued)

OTHER PUBLICATIONS

International Search Report and Written Opinion received for PCT Application No. PCT/IB2024/057702, mailed on Dec. 5, 2024, 13 pages.

*Primary Examiner* — Robert A Lynch
(74) *Attorney, Agent, or Firm* — David R. Crichton; Leo B. Kriksunov

(57) ABSTRACT

The present invention is directed to a sealant patch for use on or over sensitive tissue, comprising: a flat, flexible, bioresorbable substrate coated by a moisture-activated adhesive on one side thereof, wherein said adhesive is at least partially inactivated in a first portion of said patch, but remains active in peripheral areas surrounding the first portion. The adherence of the first portion to the tissue is weaker versus adherence in the peripheral areas. The adhesive in the first portion is fully or partially inactivated or pre-reacted prior to application of the sealant patch to the tissue.

14 Claims, 12 Drawing Sheets

(56) References Cited

U.S. PATENT DOCUMENTS

| 10,314,936 | B2 | 6/2019 | Hoogenboom et al. |
|---|---|---|---|
| 10,751,441 | B2 | 8/2020 | Bender et al. |
| 11,058,796 | B2 | 7/2021 | D'agostino et al. |
| 2010/0069927 | A1 | 3/2010 | Clark et al. |
| 2011/0045047 | A1 | 2/2011 | Bennett |
| 2013/0019569 | A1* | 1/2013 | Epstein ............... A61F 13/0276 |
| | | | 53/452 |
| 2020/0337908 | A1 | 10/2020 | Long et al. |
| 2021/0137628 | A1 | 5/2021 | Robinson et al. |
| 2021/0252185 | A1* | 8/2021 | Veruva .................. A61L 15/225 |
| 2022/0126000 | A1 | 4/2022 | Preiss-bloom et al. |
| 2022/0331475 | A1 | 10/2022 | Nativ et al. |

* cited by examiner

ABSORBABLE DRESSINGS FOR SEALING SENSITIVE NEURAL TISSUE AND DURA MATTER

FIELD OF THE INVENTION

The present invention relates to absorbable sealant patches, designs, or pads for applying to injured and/or surgically repaired dural defects with underlying and exposed sensitive neural tissues to minimize cerebrospinal fluid leaks and facilitate healing, particularly to patches for dural scaling.

BACKGROUND OF THE INVENTION

Dura mater refers to the membranes found between the skull and the brain and between the vertebral column and the spinal cord. Defects of the dura mater can produce a variety of undesirable consequences such as herniation, adhesion formation, cerebrospinal fluid fistulas and leaks, and infections. Duraplasty is a plastic or reconstructive operation on the dura mater. Repair of a dural defect may require application of a dural substitute (commonly referred to as a dural patch), especially, for example, when a large defect is created in the dural envelope in the course of a surgical procedure (e.g., tumor removal) or as a result of trauma.

There is a need in the repair of dural defects, particularly in materials that can reliably seal or repair the defects and that possess good adhesivity to tissue, good handling characteristics, and sealing properties. In some applications, also desirable is flexibility and absorbability of the repair patch.

Absorbable patches, e.g. hemostatic patches containing two cross-linkable components have been described, see for example U.S. Patent Application publication No. 2022/0331475 titled "Two Component Sealing Systems Including Synthetic Matrices and Biosynthetic Adhesives", by Nativ et al., disclosing a hemostatic patch comprising a porous substrate having available acidic carboxylic groups and at least a pair of co-reactive polymer reagents comprising at least one nucleophilic polyalkylene oxide-based component and at least one electrophilic polyalkylene oxide-based component, both of said components disposed on the porous substrate in a molar ratio of about 0.2 to about 0.9:1 of primary electrophilic groups to nucleophilic groups.

U.S. Patent Application publication No. 2021/0252185 "Melt Blown Dressing with Gradient Density" by Sai Veruva et al., discloses a wound dressing comprising a melt-blown multi-layered substrate having at least two major facing surfaces and a coated layer that is applied to at least one of the major facing surfaces of a sealing agent that is selected from the group consisting of co-reactive hydrogel-forming materials, one or more plasma-based hemostatic agents and combinations thereof, wherein the melt-blown substrate has a porosity gradient profile. The reference further discloses a wound dressing, wherein the polymeric material is a copolymer of glycolide and epsilon-caprolactone (Monocryl), polyglactin 910 (Vicryl) or combinations thereof.

U.S. Patent Application publication No. 2011/0045047 titled "Hemostatic implant" discloses an implant comprising: a porous substrate having a first hydrogel precursor comprising collagen applied to the porous substrate; and a film containing a second hydrogel precursor applied to the porous substrate.

U.S. Pat. No. 8,932,619 "Dural repair material" discloses a dural repair material comprising a foam layer comprising a mixture of oxidized collagen and glutaraldehyde crosslinked collagen joined to a non-porous film comprising crosslinked, oxidized collagen, and a mesh reinforcement member embedded within the non-porous film, wherein the mixture comprises a ratio of concentration of the oxidized collagen and glutaraldehyde crosslinked collagen between 1:1 and 1:5.

U.S. Pat. No. 8,381,498 "Method of manufacturing a dressing package" discloses a method of making a packaged dressing, the dressing having a width, an extent and a perimeter, the dressing comprising a skin adhering side having an affixation adhesive thereon, and a back side opposite the skin adhering side, the dressing further comprising a first terminus at one end of the extent and a second terminus at the other end of the extent, the second terminus defining an opening end for the packaged dressing, the method comprising: A) coating at least a portion of a first surface of a cover material with a detachable high tack, pressure sensitive adhesive; B) modifying the tack of at least one predetermined area of the detachable high tack, pressure sensitive adhesive in a predetermined pattern so that the at least one predetermined area becomes a tackless area bounded by unmodified high tack, pressure sensitive adhesive, and such that, following the modifying, the high tack, the pressure sensitive adhesive that was not subject to the modifying will be unmodified high tack, pressure sensitive adhesive and will include a dressing receiving area, the predetermined area being located (i) so as to correspond to and encompass at least a substantial portion of an edge of the first terminus and at least a portion of the surface of the cover material just beyond the edge of the first terminus, (ii) such that the unmodified high tack, pressure sensitive adhesive will be disposed to affix the back side of the dressing to the first surface of the cover material along most of the extent of the dressing when the back side of the dressing is brought into contact with the unmodified high tack, pressure sensitive adhesive on the first surface of the cover material in the dressing receiving area, C) forming a release island, on a first surface of a backing material, having a size and shape corresponding to at least the width, extent and perimeter of the dressing; D) sandwiching the dressing between the first surface of the cover material and the first surface of the backing material such that (i) the skin adhering side of the dressing will be in contact with and substantially correspond to the release island, (ii) substantially all of the extent of the back side of the dressing will be in contact with, and held by, the unmodified high tack, pressure sensitive adhesive in the dressing receiving area on the first surface of the cover material, (iii) a substantial portion of the edge of the first terminus of the back side of the dressing overlays the tackless area, and (iv) the unmodified high tack, pressure sensitive adhesive will form a hermetic seal encompassing at least the entire perimeter of the dressing and the tackless area.

U.S. Patent Application Publication No. 2010/0069927 "Polymeric Masking Materials for Spanning Wound Sites, and Methods of Use Thereof", discloses a method of bandaging, covering, or bridging a defect, a wound, or a void of the tissue of a patient, comprising the steps of: covering the defect, wound, or void with a first material; and covering the first material with a second material; wherein the area covered by the first material is greater than or equal to the area of the defect, wound, or void; the second material covers the area covered by the first material; and the area covered by the second material is greater than the area covered by the first material.

U.S. Patent Application Publication No. 2021/0137628 "Systems for inducing and indicating deactivation of adhesive drapes" discloses a light deactivated adhesive drape system configured to be coupled to tissue, the system comprising: a drape having an acrylic and/or polyurethane film, the film comprising: a photosensitive adhesive layer having at least one release agent, wherein the at least one release agent is configured to weaken a bond of the adhesive layer to the tissue upon exposure to at least one of a plurality of light wavelengths; and a photosensitive pigment layer having at least one photoinitiator, wherein the at least one photoinitiator is configured to change a color of the photosensitive pigment layer upon exposure to the at least one of the plurality of light wavelengths.

U.S. Patent Application Publication No. 2020/0337908 "Systems and methods for coupling a wearable therapy system to a dressing" discloses a radiation deactivated adhesive drape having an inner surface configured to be coupled to tissue and an outer non-tissue facing surface, the drape comprising: a switchable adhesive disposed on the outer drape surface, the switchable adhesive being configured to adhere the drape to a medical therapy unit, the switchable adhesive including: a radiation-sensitive adhesive layer having at least one release agent disposed within the adhesive layer, wherein the at least one release agent is configured to weaken a bond of the adhesive layer to a surface upon exposure to at least one of a plurality of radiation wavelengths; and a removable blocking layer having at least one blocking agent disposed within the blocking layer, wherein the blocking layer blocks the at least one of a plurality of radiation wavelengths from exposing the photosensitive adhesive layer.

U.S. Pat. No. 7,396,976 "Easy-to-peel securely attaching bandage" discloses a bandage, comprising: a. a backing layer; b. a plurality of portions of the backing layer containing an adhesive appointed for contact with skin of a bandage wearer; c. a plurality of pockets containing an adhesive-inactivating ingredient disposed in the adhesive-containing portions of the backing layer; d. said pockets being operative to rupture upon application of pressure or scratching by the bandage wearer, thereby releasing said adhesive-inactivating ingredient; e. said adhesive-inactivating ingredient, upon release, being delivered at the skin contacting interface of said adhesive, reducing adhesive bond strength and enabling pain-free removal of said bandage; f. a central wound-contacting absorbent pad bonded by hot melt glue or strong adhesive to said backing layer; and g. wherein said backing layer is embossed with pockets, filled with said adhesive-inactivating ingredient and sealed with a second polymeric layer prior to the application of said adhesive.

SUMMARY OF THE INVENTION

The present invention, in some embodiments, is directed to a sealant patch for use on or applied over and around sensitive tissue, comprising: a flat, flexible, bioresorbable substrate coated by a moisture-activated adhesive on one side thereof, wherein said adhesive is at least partially inactivated in a first portion of said patch, but remains active in peripheral areas surrounding the first portion. The degree of adherence of the first portion to the underlying tissue is weaker relative to the degree of adherence in the peripheral overlaid areas. The adhesive in the first portion is fully or partially inactivated or pre-reacted prior to application of the sealant patch to the tissue. The adhesive can comprise an electrophile and a nucleophile, wherein the electrophile can be PEG-Succinimidyl Glutarate (PEG-SG) compound and the nucleophile can be one or more PEG-amine compounds.

The present invention, in some embodiments, is directed to a method of making the sealant patch comprising the steps of: coating a substrate with a moisture-activated adhesive on one side thereof; applying an aqueous solution onto a first portion of said sealant patch; at least partially inactivating the adhesive on said first portion; and drying the sealant patch.

The present invention, in some embodiments, is directed to a kit comprising: a unified packaging; and, disposed inside said packaging a flat, flexible, bioresorbable substrate coated by a moisture-activated adhesive on one side thereof, a manual dropper containing an inactivating liquid, configured for application onto the substrate.

DETAILED DESCRIPTION OF PREFERRED EMBODIMENTS

Figure 1A:
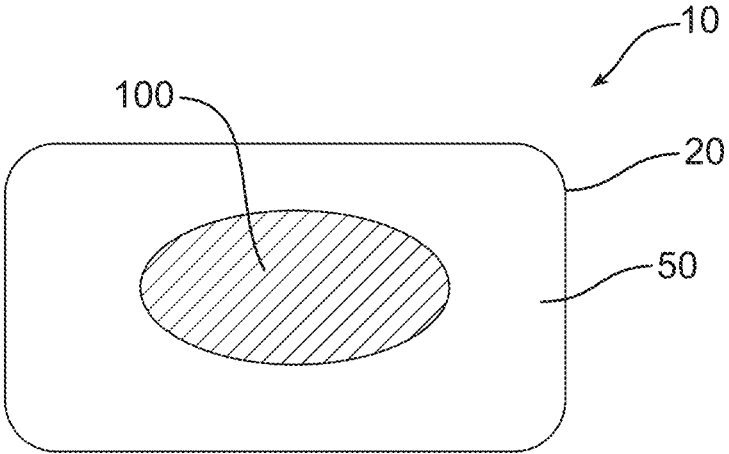
FIG. 1A illustrates a top view a schematic representation of an embodiment of the dural sealant patch.

The present invention relates to wound dressing to seal leaks/bleeds or close/repair tissues having inactivating region(s) and adhering region(s) of a sealant/adhesive patch in order by sticking along the edges, wherein one or more central regions are provided with materials that are rendered non-reactive with potential sensitive tissues or structures. For example, a dural sealing adhesive patch can be used to seal cerebrospinal fluid leaks and dural tears closure, however the unintended "sticking" of the patch to exposed nerves, roots or brain/spinal cord tissue under the dura can pose clinical risks such as nerve tethering, impingement, or other adhesions-associated complications. Currently, this method requires use of an artificial or autologous inlay products to serve as barrier for protection, whereas the current invention provides a method to directly inactivate the "sticky" adhesive portion of the patch that will subsequently not react/adhere to sensitive tissues or structures of interest. The objective of this invention is to solve an unmet need for primary sealing and tissue repair/closure and simultaneously mitigate a clinical risk. Advantageously, no additional shielding material is added such as a pledget or film. Advantageously, the risk of adherence to sensitive nerve/brain/tissue structures, especially related to clinical challenges with large durectomy or dural defects, is mitigated by the use of the embodiments of the present invention.

Advantageously, for use with the sensitive tissues, embodiments of the present invention prevent sticking of the patch to the sensitive tissue (such as nerves or neuronal tissue), though the patch exhibits a suitable degree of tissue adherence to the areas around (such as dura), without patterned coating or a pledget of non-sticky material in the middle. In the inventive embodiments, a patch having a moisture activated adhesive over all tissue-facing surface is formed by inactivating or pre-reacting the adhesive in the center of the patch.

Briefly, in some embodiments, the present dural sealant patch comprises a flexible, areal, absorbable substrate coated on a tissue-facing surface thereof with moisture-activatable adhesive, that is at least partially inactivated in a first portion of the patch to prevent or weaken sticking/adhering of the first portion to dura matter. For purposes of this disclosure. In general usage. "deactivated" and "inactivated" are often used interchangeably to mean that something has been rendered inactive or non-functional. The term "deactivated" generally implies the removal or neutralization of an active or functional aspect of a substance. For example, in the context of chemical reactions or processes, deactivation may refer to reducing or eliminating the catalytic properties of a catalyst. In this case, "deactivation" or "inactivation" occurs when the tissue reactive and adhering functional groups in the adhesive formulations am significantly diminished or functionally not available for reaction. Such deactivation can occur by reaction with another agent that consume via reaction all of these tissue reactive groups.

Figure 1B:
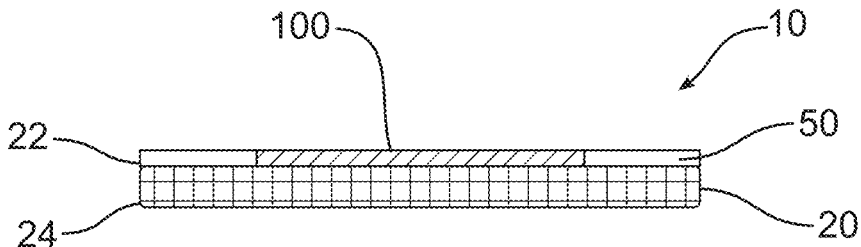
FIG. 1B illustrates a side cross-sectional view a schematic representation of an embodiment of the dural sealant patch.

Referring now to FIGS. 1A and 1B, a schematic representation of an embodiment of the inventive dural sealant patch 10 is presented, with FIG. 1A showing a top view and FIG. 1B showing a side cross-sectional view. Patch 10 comprises a flexible, thin, flat, absorbable, optionally porous substrate 20 having a tissue facing side 22 and an opposite uncoated side 24. Tissue facing side 22 is coated by a moisture activated adhesive coating 50. In a first portion of patch 10 adhesive 50 on tissue facing side 22 is at least partially inactivated forming an inactivated first portion 100.

Figure 2A:
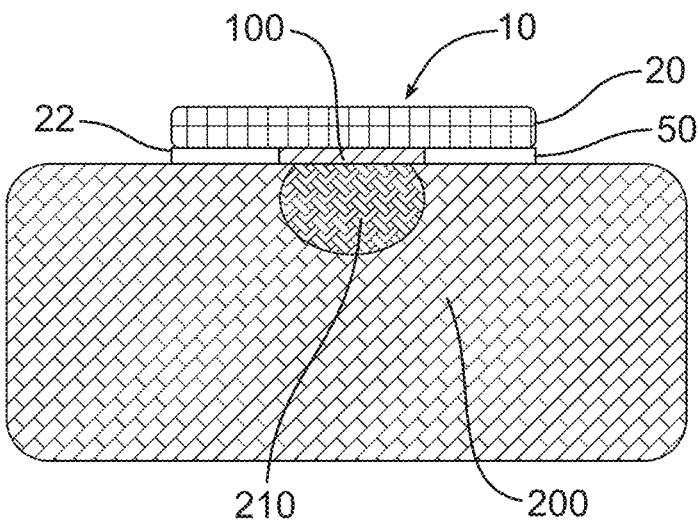
FIG. 2A presents a schematic representation of an embodiment of the dural sealant patch applied to tissue, showing a side cross-sectional view.

Referring to FIG. 2A, a schematic representation of an embodiment of the inventive dural sealant patch 10 is presented applied to a dural tissue 200 (or over a tear in the dural tissue) with the sensitive neural tissue 210 in the center. As shown in a schematic side cross-sectional view, patch 10 is positioned with tissue facing side 22 facing sensitive neural tissue 210 and dural tissue 200, and with inactivated first portion 100 positioned against sensitive tissue 210. Moisture activated adhesive coating 50 is shown to be adhering to dural tissue 200.

Advantageously, when applying onto or over dural matter and dural defects, patch 10 is configured to strongly adhere to surrounding dural tissue 200, but not as strongly adhering (or not at all adhering) to sensitive neural tissue 210 itself, or in the immediate vicinity of the sensitive neural tissue 210, thus decreasing the potential for neural damage, while still sealing leaks, closing dura and also protecting underlying sensitive tissue.

Figure 2B:
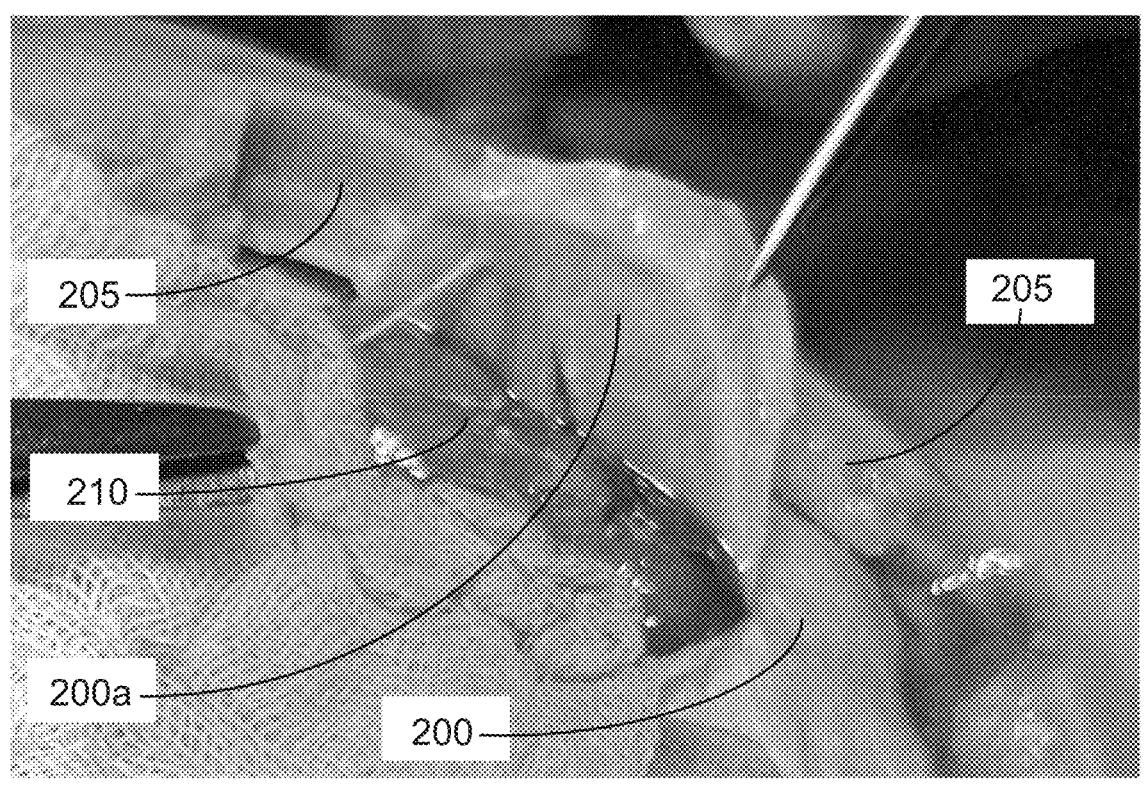
FIG. 2B shows a photographic image of dura, bone, dural flap, sensitive neural tissue.
Figure 2C:
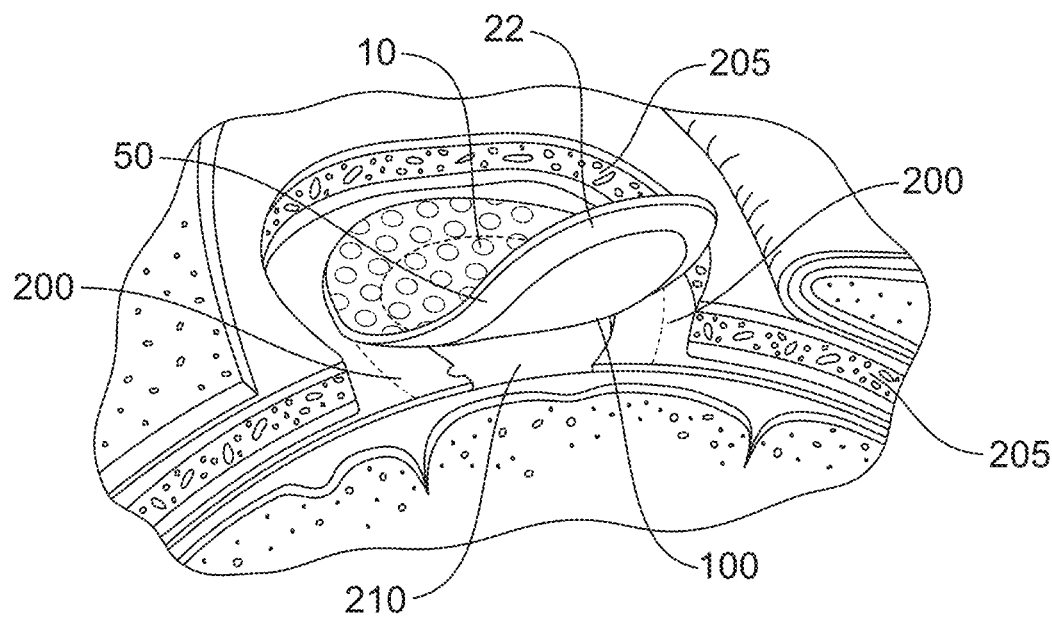
FIG. 2C shows a schematic representation in a perspective view of application of patch 10 to dural and sensitive neural tissue.

FIG. 2B shows photographic image of dura 200, bone 205, dural flap 200a, sensitive neural tissue 210. FIG. 2C shows a schematic representation in a perspective view of application of patch 10, with dura 200, bone 205, sensitive neural tissue 210. Patch 10 is shown partially applied, positioned with tissue facing side 22 facing sensitive neural tissue 210 and dural tissue 200, and with inactivated first portion 100 positioned against sensitive tissue 210 and optionally against immediately surrounding dural tissue 200. Moisture activated adhesive coating 50 is shown to be adhering to dural tissue 200.

Figure 2D:
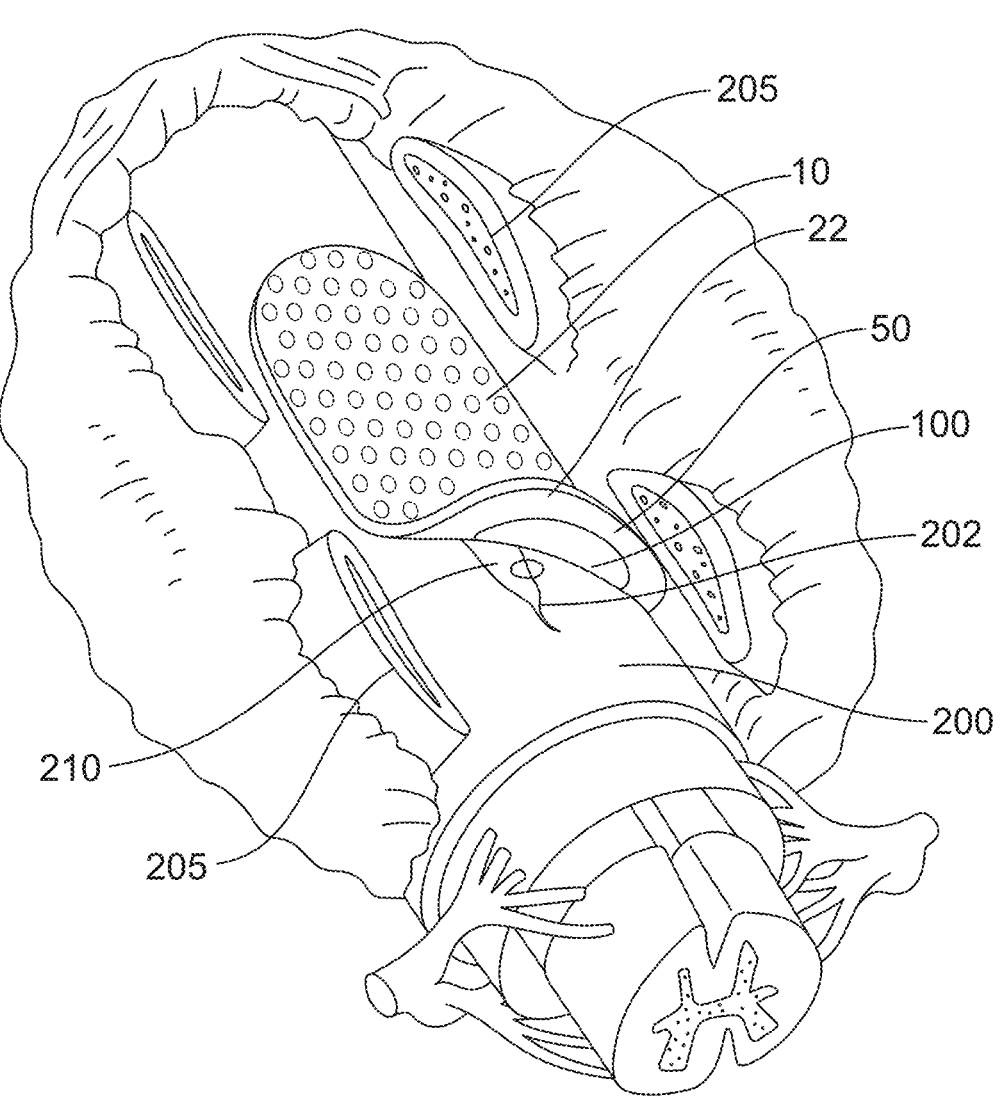
FIG. 2D shows a schematic representation in a perspective view of application of patch 10 to dural tear and sensitive neural tissue.

FIG. 2D shows a schematic representation in a perspective view of application of patch 10, with dura 200, dural tear 202, bone 205, sensitive neural tissue 210. Patch 10 is shown partially applied, positioned with tissue facing side 22 facing sensitive neural tissue 210 and dural tissue 200, and with inactivated first portion 100 positioned against sensitive tissue 210 and optionally against immediately surrounding dural tissue 200. Moisture activated adhesive coating 50 is shown to be adhering to dural tissue 200.

Figure 3A:
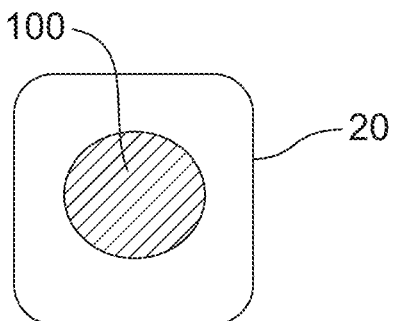
FIG. 3A illustrates a square-shaped substrate having a circular shaped inactivated first portion.
Figure 3B:
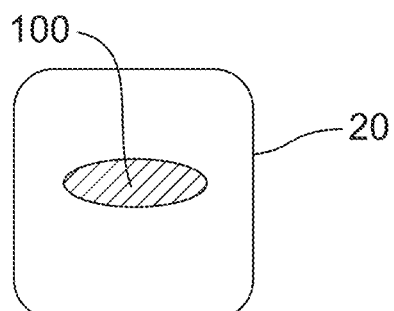
FIG. 3B illustrates a square-shaped substrate having an oval shaped inactivated first portion.
Figure 3C:
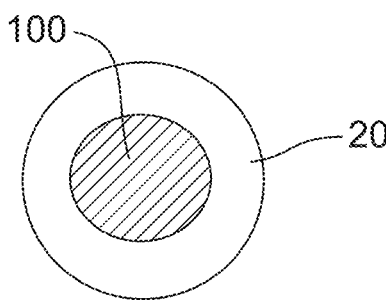
FIG. 3C illustrates a round-shaped substrate having a round shaped inactivated first portion.
Figure 3D:
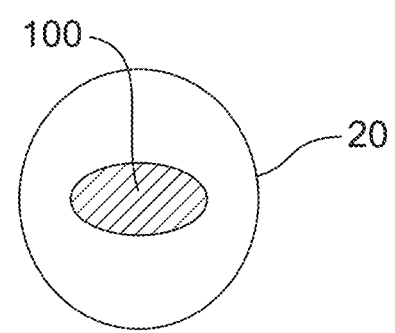
FIG. 3D illustrates a round-shaped substrate having an oval shaped inactivated first portion.
Figure 3E:
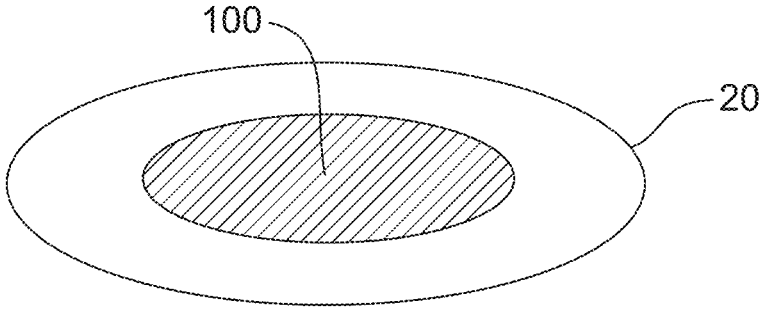
FIG. 3E illustrates an oval-shaped substrate having an oval shaped inactivated first portion.

A variety of shapes and forms of patch 10 can be utilized. FIGS. 1A and 1B show rectangular substrate 20 and oval shaped inactivated first portion 100. FIG. 3 shows several potential shapes and combinations in a schematic top view from tissue facing side of patch 10. FIG. 3A shows square shaped substrate 20 and circular or round shaped inactivated first portion 100. FIG. 3B shows square shaped substrate 20 and oval shaped inactivated first portion 100. FIG. 3C shows round shaped substrate 20 and round shaped inactivated first portion 100. FIG. 3D shows round shaped substrate 20 and oval shaped inactivated first portion 100. FIG. 3E shows oval shaped substrate 20 and oval shaped inactivated first portion 100.

Coloration of Inactivated First Portion

In certain embodiments, inactivating liquid 60 further comprises a biocompatible dye that provides coloration of inactivated first portion 100 after liquid 60 is applied to moisture activated adhesive coating 50. Coloration of inactivated first portion 100 can be a distinct color, such as blue, red, yellow, etc., or a contrasting shade, or weakening or bleaching or changing tone of previously present color, or any visibly differentiating look of inactivated first portion 100 as compared to the rest of substrate 20 and or still active moisture activated adhesive coating 50. Advantageously, such visible marking of inactivated first portion 100 is helping healthcare practitioner when applying patch 10 onto areas of dural tissue 200 and underlying sensitive neural tissue 210.

In one embodiment, coloration or dye on inactivated first portion 100 is visible on tissue facing side 22 only. In another embodiment, coloration or dye on inactivated first portion 100 is visible on opposite uncoated side 24 only. In yet another embodiment, coloration or dye on inactivated first portion 100 is visible on both tissue facing side 22 and on opposite uncoated side 24. In an alternative embodiment, coloration or dye tone is different on tissue facing side 22 versus on opposite uncoated side 24, also indicating which side is tissue facing side 22.

Coloration or dye on inactivated first portion 100 can be exactly the same shape and dimensions as inactivated first portion 100 or somewhat larger, such as 5-30% larger, such as 10%, 20% larger.

In some embodiments, intensity of coloration or dye on inactivated first portion 100 is indicative of the extent of inactivation of moisture activated adhesive coating 50 in that portion 100. As described in embodiments relating to gradient inactivated first portion 100, whereby the center of inactivated first portion 100 is inactivated more than periphery of first portion 100, coloration or dye on inactivated first portion provides a visible indication of the degree of inactivation, whereby coloration or dye or bleaching is higher where in the center of inactivated first portion 100 and lower on the periphery of first portion 100.

Figure 4A:
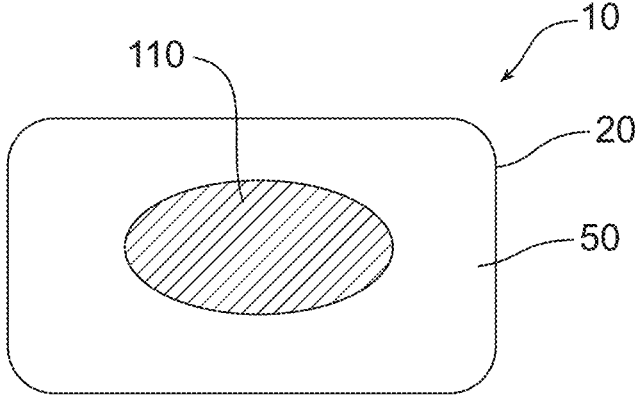
FIGS. 4A and 4B present embodiments of the dural sealant patch in a schematic top view.
Figure 4B:
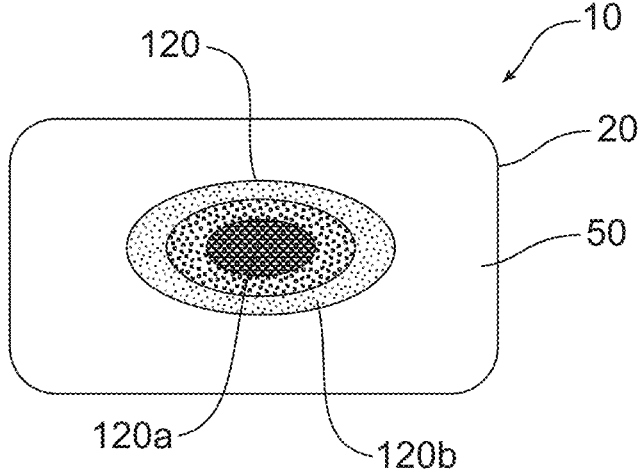

FIG. 4A shows patch 10 with coloration or dye 110 applied to substrate 20 and having the same shape and dimensions as underlying inactivated first portion. FIG. 4B shows patch 10 with intensity of coloration or dye 120 changing from higher in the first portion 120a to lower in the peripheral portion 120b, indicative of gradient inactivated first portion, with most inactivated adhesive in the first portion 120a and least inactivated adhesive in the peripheral portion 120b.

Materials: Substrate

Substrate 20 can be any biocompatible, preferably bioabsorbable material, such as synthetic or natural polymer. In some embodiments, substrate 20 compromises gelatin, collagen, polyethylene glycol, oxidized cellulose, carboxymethyl cellulose, lactide, glycolide, epsilon-caprolactone, copolymers of lactide, glycolide, epsilon-caprolactone, and polydioxanone, and combinations thereof. In one embodiment, it comprises poliglecaprone 25, a copolymer of glycolide and epsilon-caprolactone. Substrate 20 can be in a form of extruded film, woven, non-woven, melt-blown, etc. form, and combinations thereof. In some embodiments substrate 20 comprises a single layer of material. In alternative embodiments, substrate 20 comprises multiple layers of the same material. In certain embodiments, substrate 20 comprises a multilayer construct of different biocompatible materials, such as comprising gelatin or collagen layer and a synthetic polymer layer. The layers can be structurally integrated via ultrasonic welding, needle punching, heat welding, chemical attachment, suture attachment or combinations thereof.

In a preferred embodiment substrate 20 is a porous, thin, flexible, bioabsorbable sheet made of synthetic polymer such as copolymer of glycolide and e-caprolactone, comprising multiple layers of melt-blown polymer.

Materials: Adhesive Coating

In one embodiment, moisture activated adhesive coating 50 comprises at least one reactive, cross-linkable component and more preferably at least two reactive, cross-linkable components that are co-reactive with each the other. In one embodiment, moisture activated adhesive coating 50 comprises an electrophile and a nucleophile. The electrophile can be, for example, polyethylene glycol (PEG) derivatized with a reactive group, such as PEG-Succinimidyl Glutarate (PEG-SG or PEG-NHS). The nucleophile can be, for example, PEG-amine (PEG-NH2), or a protein such as albumin, gelatin, collagen, etc. In some embodiments, electrophile and nucleophile are in approximately stoichiometric mix. In alternative embodiments, stoichiometrically there is more electrophile. In one embodiment, there is only electrophile such as PEG-NHS in moisture activated adhesive coating 50 for reactivity with tissue and or with substrate 20, which can contain nucleophile groups, such as substrate 20 containing gelatin.

In one embodiment, moisture activated adhesive coating 50 comprises fibrinogen and thrombin. In one embodiment, moisture activated adhesive coating 50 comprises isocyanate adhesive. In one embodiment, moisture activated adhesive coating 50 comprises polyurethane adhesive.

In other embodiments, moisture activated adhesive coating 50 comprises one or more of electrophilically activated polyoxazoline (EL-POX) and nucleophilically activated polyoxazoline (NU-POX). These reactive compounds are described in U.S. patents: U.S. Ser. No. 10/314,936, U.S. Pat. No. 9,416,228, U.S. Ser. No. 10/751,441, which are incorporated herein by reference in their entirety.

Materials: Inactivating Liquid

According to embodiments of the present invention, inactivating liquid 60 comprises water, aqueous solutions, aqueous buffer solutions, water-solvent mixtures such as water-alcohol mixtures, such as water-ethanol mixtures, and combinations thereof. In one embodiment, inactivating liquid 60 comprises water—ethanol mixture, containing 5, 10, 20, 30, 40, 50, 60, 70% of water. Other rapidly evaporating solvents can be used, such as methanol, acetone, etc. In one embodiment, inactivating liquid 60 comprises water—ethanol mixture and alkaline buffer, containing 5, 10, 20, 30, 40, 50, 60, 70% of water.

In one embodiment, inactivating liquid 60 comprises alkaline buffer, such as aqueous phosphate buffer, borate buffer, carbonate based buffer, or similar, having pH of about 7.5-12, more preferably 8-10, for facilitating rapid reaction between nucleophile and electrophile in adhesive coating 50.

In one embodiment, inactivating liquid comprises a solution of nucleophile, such as albumin, configured to react with PEG-NHS in adhesive coating 50.

In one embodiment, inactivating liquid comprises a surfactant.

Methods of Making the Patch

According to embodiments of the present invention dural sealant patch 10 is formed as follows. Substrate 20 is provided in a form of rolls or sheets and then is optionally pre-cut to desired size. Either pre-cut of non-pre-cut substrate 20 material is then coated with moisture activated adhesive coating 50 on one side of substrate 20 (on tissue facing side 22). The coating is performed by any method known to a skilled artisan, such as spray coating, ultrasonic nozzle spray coating, dip or immersion coating, printing coating, gravure coating, powder coating with thermal fixation, compression coating, pattern coating, etc. The coating is performed so as to avoid deactivating adhesive coating 50. In some embodiments adhesive coating 50 components applied separately in layers or are printed in spatially separate and interdigitated micro-zones. In some embodiments adhesive coating 50 components are applied jointly or sequentially in a non-aqueous solvent that is then removed by evaporation or drying. In some embodiments adhesive coating 50 components are applied jointly or sequentially as powders and then fixated on substrate 20 thermally by at least partial melting.

After applying adhesive coating 50 to large sheets of non-pre-cut substrate 20 material, this material is optionally cut to final size of patch 10. Alternatively, substrate 20 material can be cut to final size of patch 10 after forming inactivated first portion 100. If adhesive coating 50 was applied to already pre-cut substrate 20 material, this step is not needed.

Figure 5A:
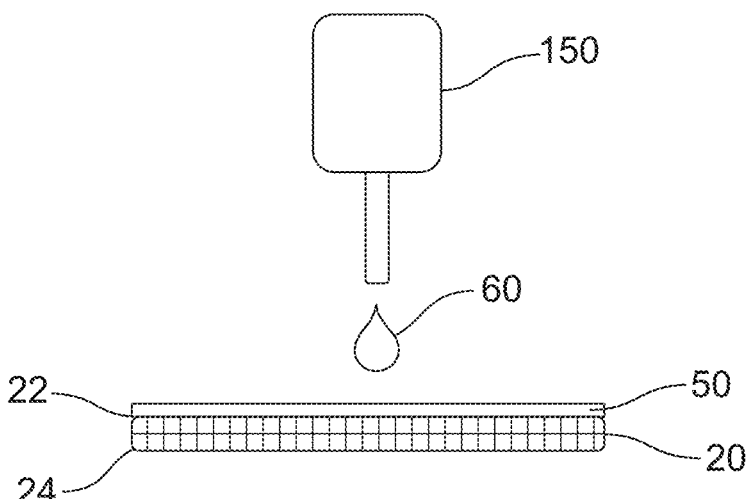
FIG. 5A illustrates a method of forming an inactivated first portion in a schematic cross-sectional view by applying a metered amount of inactivating liquid applied from tissue facing side.
Figure 5B:
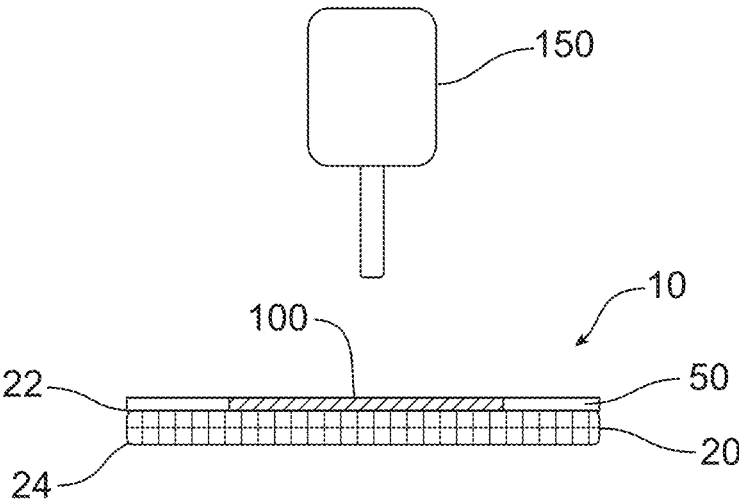
FIG. 5B illustrates an adhesive coating that has been at least partially inactivated.

FIG. 5A shows a schematic cross-sectional view of substrate 20 having adhesive coating 50 facing upwards positioned under a metered liquid dispenser 150 that dispenses a metered amount of inactivating liquid 60 onto first portion of substrate 20 tissue facing side 22. FIG. 5B shows that after inactivating liquid 60 has distributed over first portion of substrate 20 at rendered adhesive coating 50 at least partially inactivated, inactivated first portion 100 is formed in the first portion of patch 10. Inactivating liquid 60 can then be allowed to evaporate by drying, vacuum drying, heated facilitated drying, etc.

Figure 5C:
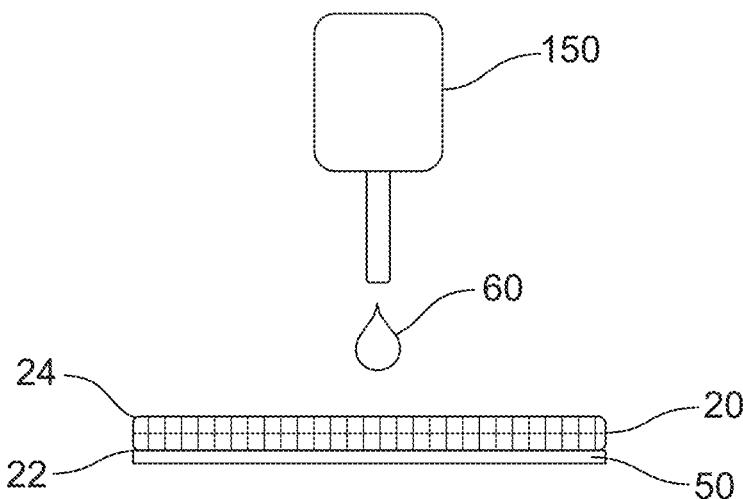
FIG. 5C illustrates a method of forming inactivated first portion by application of inactivating liquid from an opposite side.
Figure 5D:
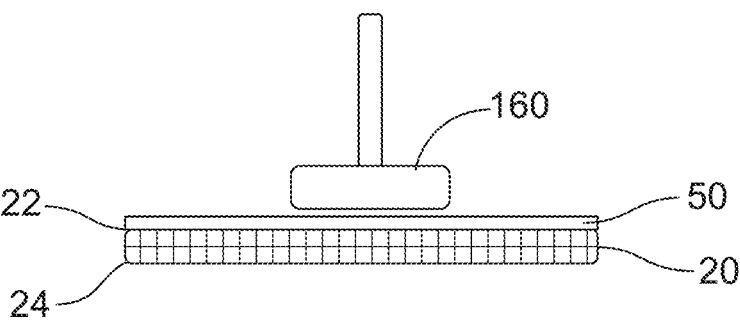
FIG. 5D illustrates a steam dispenser positioned in close proximity to adhesive coating.

While FIGS. 5A and 5B show applied from tissue facing side 22 when this side is facing upwards, FIG. 5C shows that for porous substrate 20, inactivating liquid 60 can be applied from opposite side 24. As shown in FIG. 5C, porous substrate 20 with adhesive coating 50 is positioned facing downwards, i.e. with tissue facing side 22 facing downwards. Porous substrate 20 is positioned under a metered liquid dispenser 150 that dispenses a metered amount of inactivating liquid 60 onto first portion of substrate 20 opposite side 24 that is facing upwards. Inactivating liquid 60 is then penetrating through porous substrate 20 to reach adhesive coating 50 and form inactivated first portion 100 is formed in the first portion of patch 10.

As shown in FIG. 5), in one embodiment, a steam dispenser 160 is positioned in close proximity to adhesive coating 50. Steam dispenser 160 is sized to be close to dimensions of to be formed inactivated first portion 100. Dispensing steam of inactivating liquid 60, which can be water, aqueous solution, water-ethanol mixture, or similar, onto adhesive coating 50 is then rendering adhesive coating 50 at least partially inactivated, and inactivated first portion 100 is formed in the first portion of patch 10.

Figure 5E:
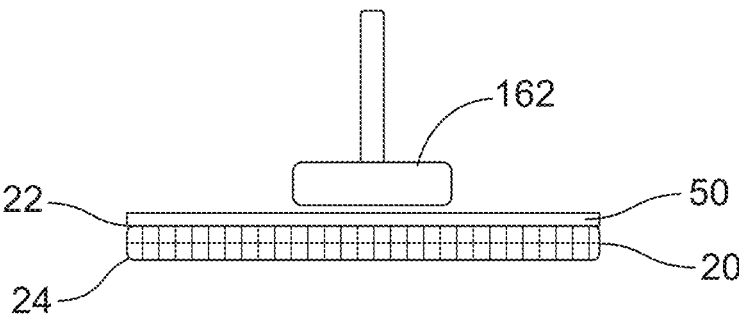
FIG. 5E illustrates a heated arm that is positioned in close proximity to adhesive coating.

As shown in FIG. 5E, in one embodiment, a heated arm 162 is positioned in close proximity (as shown) to or touching adhesive coating 50 (not shown). Heated arm 162 is sized to be close to dimensions of to be formed inactivated first portion 100. Heating heated arm 162, for example by electric energy, results in heating adhesive coating 50 immediately under heated arm 162, and thermal inactivation of adhesive coating 50, rendering adhesive coating 50 at least partially inactivated. Inactivated first portion 100 is then formed in the first portion of patch 10.

Figure 6:
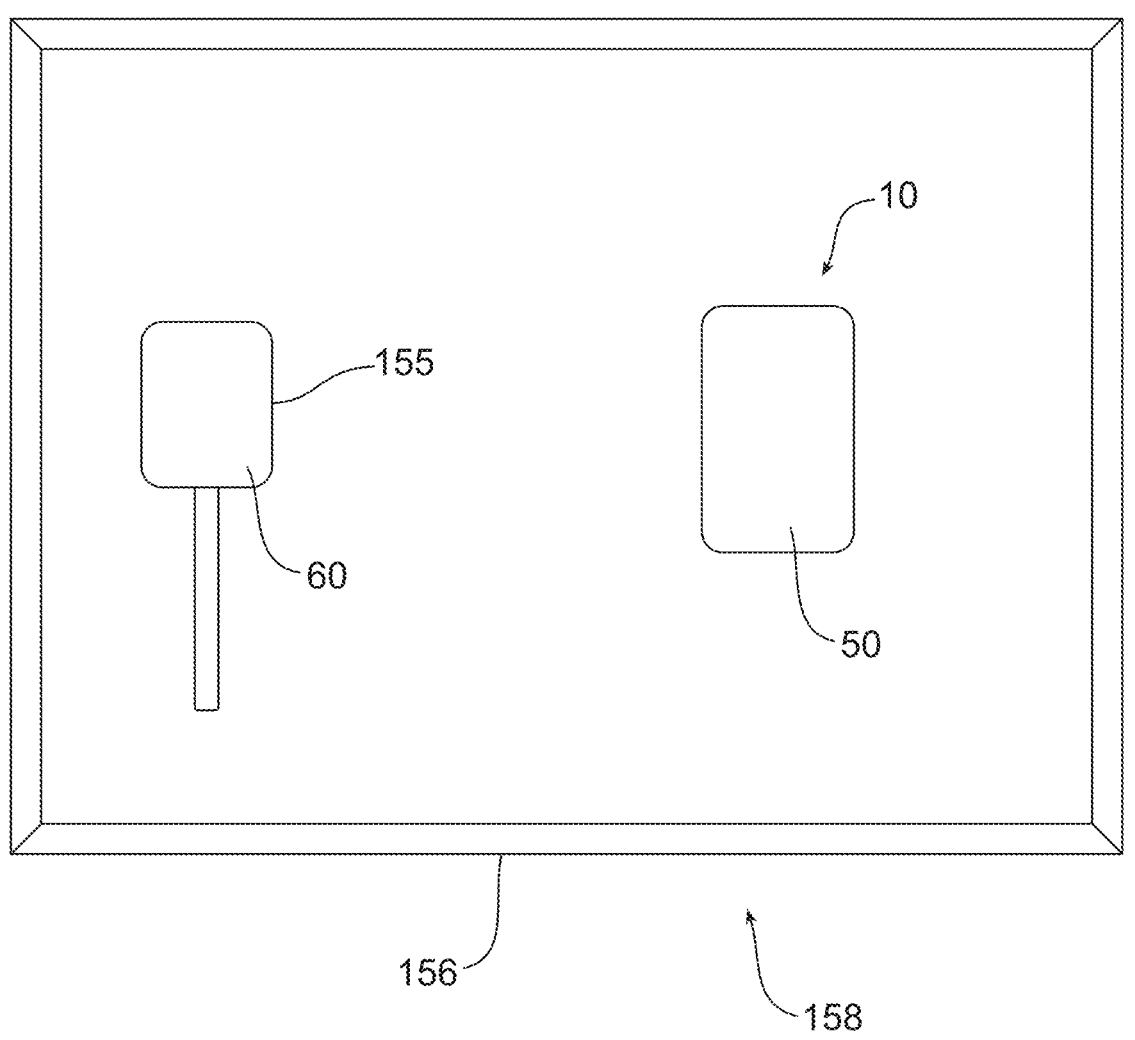
FIG. 6 illustrates a kit comprising a unified packaging containing at least one patch co-packaged with a manual dropper containing inactivating liquid.

Referring now to FIG. 6, a kit 158 comprising a unified packaging 156 containing at least one patch 10 co-packaged with a manual dropper 155 containing inactivating liquid 60. In this embodiment, a healthcare practitioner, prior to using patch 10, opens unified packaging 156 and then uses manual dropper 155 to apply inactivating liquid 60 onto adhesive coating 50 thus forming inactivated first portion 100. Such preparation of patch 10 is preferably performed immediately before use of patch 10 in medical, surgical procedure, such within 1, 2, 5, 10, 30, 60 minutes or within 1, 2, 3, 6, 12 hours, such as use within 10 minutes, 30 minutes, 1 hour, 2 hours, of preparing patch 10.

Example 1

A substrate made of flat, porous, multi-layer melt-blown non-woven (MBNW) polymer that comprised a copolymer of glycolide and epsilon-caprolactone was tested uncoated by any cross-linkable hydrogel forming active materials. The uncoated substrate was then tested by adding alcohol-based inactivating solutions of water to test absorbency and distribution on hydrophobic substrate. The liquid was added drop-wise into the first portion of the substrate to simulate creation of the inactivated first portion 100. The liquid was then allowed to evaporate and the substrate was dried at ambient temperature of 20-25° C. Depending on solvent concentration, the liquid evaporated as quickly as within 5 minutes, whereas lower concentrated alcohol solutions were left to dry overnight for at least 12 hours. Coated substrates with same technique were dried under vacuum for up to 48 hours, removed all traces of alcohol solvent (<10 ppm).

When tested with purified water, water alone failed to rapidly absorb on the hydrophobic material. However, when tested with solution made of water plus ethanol, the alcohol mixture readily absorbed into the substrate. In one embodiment, a viscosifier was added to slow down the diffusion of liquid and create a gradient of inactivation.

Referring to FIG. 7, results of testing are presented, showing the MBNW substrate after application of the inactivating liquid. The conditions of the testing are shown in Table 1.

TABLE 1

Figure 7A:
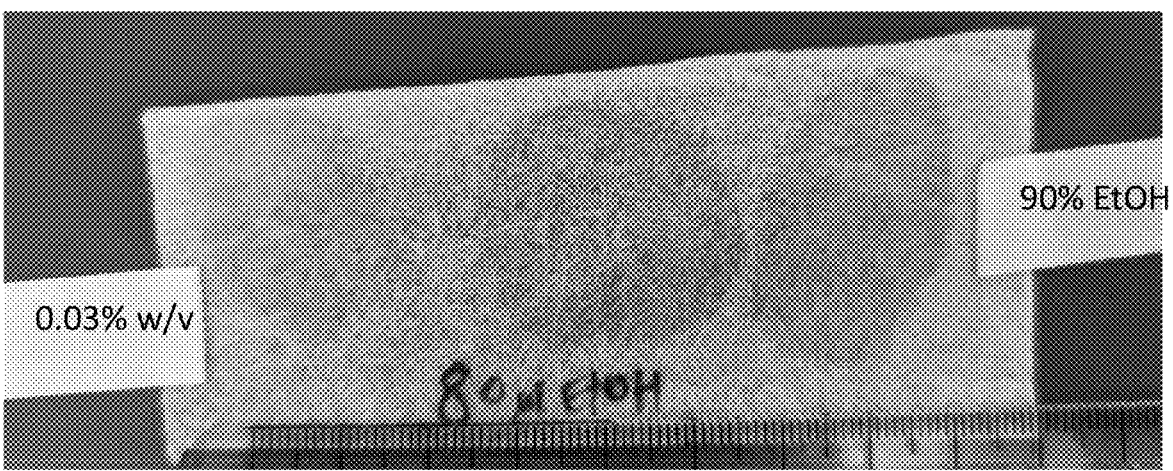
FIGS. 7A, 7B and 7C illustrate images of substrates that were tested with various inactivating fluid compositions.
Figure 7B:
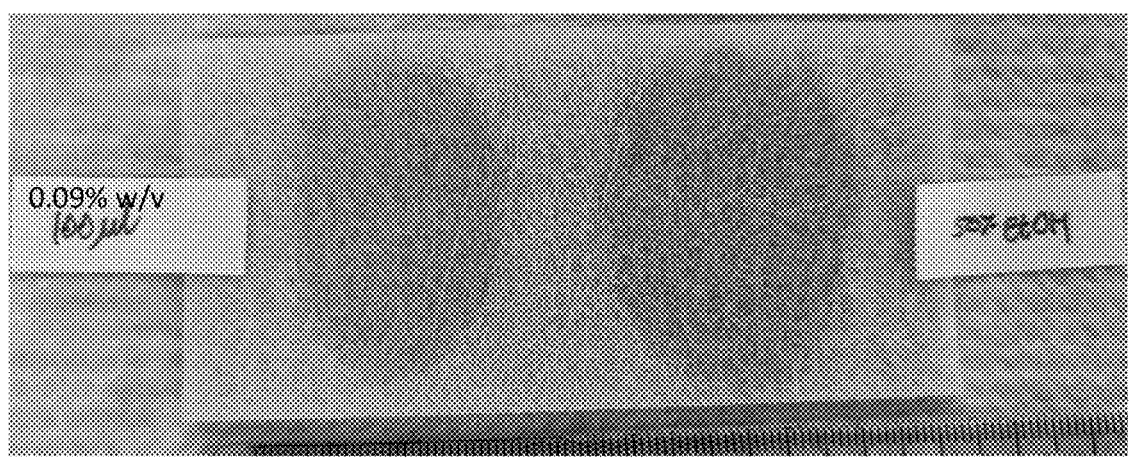
Figure 7C:
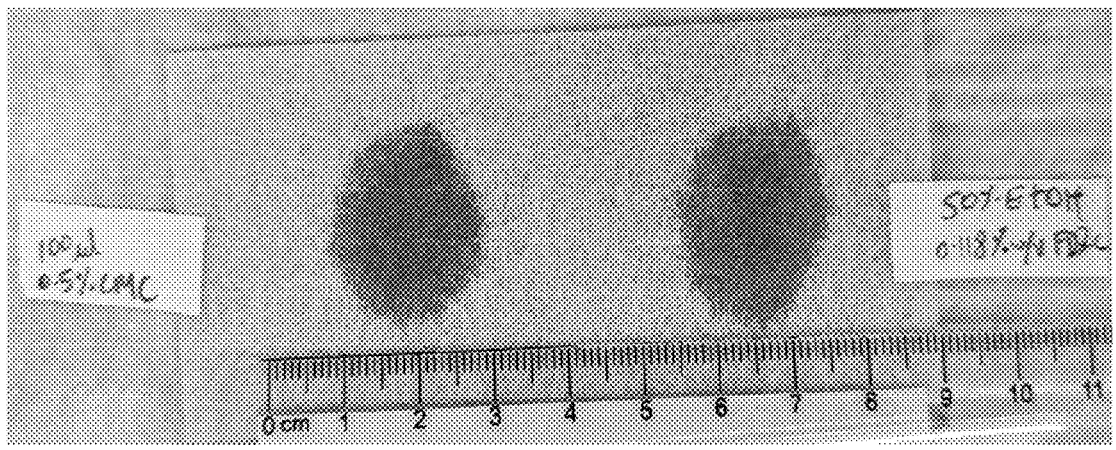

| | | Conditions of testing | | |
| --- | --- | --- | --- | --- |
| | Volume | FD&C dye | Ethanol | CMC |
| FIG. 7A | 80 µl | 0.03 w/v % | 90% | 0 |
| FIG. 7B | 100 µl | 0.09 w/v % | 50% | 0 |
| FIG. 7C | 100 µl | 0.118 w/v % | 50% | 0.5 w/v % |

FIG. 7A shows MBNW substrates after application of 80 µl of 10% water-90% ethanol solution, also containing FD&C dye at 0.03 w/v %.

FIG. 7B shows MBNW substrates after application of 100 µl of 50% water-50% ethanol solution, also containing FD&C dye at 0.09 w/v %.

FIG. 7C shows MBNW substrates after application of 100 µl of 50% water-50% ethanol solution, also containing FD&C dye at 0.118 w/v %, and further containing viscosifier carboxymethylcellulose CMS at 0.5 w/v %. As seen from the intensity of coloration, a gradient of distribution of the inactivating liquid is forming, with more in the center of the patch.

The testing shows that water-ethanol based inactivating liquid forms well-defined areas on MBNW substrates, and viscosifier slows down spread of the inactivating liquid while helping to form a radial gradient of inactivating liquid distribution.

We claim:

1. A tissue adhering sealant patch comprising:
   a) a flat, flexible, bioresorbable substrate having two major facing surfaces, including a tissue-facing side and an opposite side, and
   b) a moisture-activated and tissue reactive adhesive having a measurable degree of tissue adhesion that has been applied onto the tissue-facing side,
   wherein
   1) at least a first portion of the moisture-activated and tissue reactive adhesive on the tissue-facing side has been at least partially deactivated,
   2) while a second portion of the moisture-activated and tissue reactive adhesive on the tissue-facing side
   (i) has not been deactivated and
   (ii) provides a desired degree of tissue adhesion between the substrate and at least a portion of a tissue surface that underlays the substrate which is located in proximity to a sensitive or compromised tissue surface that is covered by at least a portion of substrate having deactivated tissue reactive adhesive.

2. The sealant patch of claim 1, wherein the degree of tissue adherence of the first portion of the substrate to the tissue is less than the degree of tissue adherence in the second portion of the substrate.

3. The sealant patch of claim 1, wherein the adhesive in the first portion is fully deactivated or fully pre-reacted prior to application of the sealant patch to tissue.

4. The sealant patch of claim 1, wherein the adhesive in the first portion, after being subjected to a deactivating agent, retains 10% to 50% of its original measurable degree of tissue adhesion.

5. The sealant patch of claim 1, wherein the first portion has a measurable color differential relative to the second portion.

6. The sealant patch of claim 1, wherein the substrate contains fibers or filaments comprising a copolymer of glycolide and epsilon-caprolactone.

7. The sealant patch of claim 1, wherein the tissue reactive adhesive comprises a blend of at least one compound having electrophilic groups and at least one compound having nucleophilic groups.

8. The sealant patch of claim 7, wherein the at least one compound having electrophilic group is polyalkylene oxide compound and at least one compound having nucleophilic groups is a polyethylene glycol (PEG) molecule with an amine functional group (PEG-amine).

9. The sealant patch of claim 1, wherein the adhesive is fibrinogen and thrombin; isocyanate based adhesive; or polyurethane based adhesive.

10. The sealant patch of claim 1, wherein the adhesive in the first portion is deactivated so that the measurable change in the degree of tissue adhesion after deactivation is greatest in a central region of the substrate and decreases as the degree of tissue adhesion is measured after deactivation in a peripheral region of the substrate.

11. The sealant patch of claim 10, wherein an observable color difference on the substrate indicates the change in the degree of tissue adhesion after deactivation.

12. A method of making the sealant patch of claim 1 comprising the steps of:

a) Coating the substrate with the moisture-activated and tissue reactive adhesive on the at least one major surface thereof;

b) Applying an aqueous solution onto the first portion of said sealant patch to at least partially deactivate the tissue reactive adhesive on said first portion; and c) drying the sealant patch.

13. A method of making the sealant patch of claim 1 comprising the steps of:

a) Coating the substrate with the moisture-activated and tissue reactive adhesive on the at least one major surface thereof;

b) Applying a water or a water-ethanol steam to the first portion of said sealant patch to at least partially deactivate the adhesive on said first portion; and c) Drying the sealant patch.

14. A method of making the sealant patch of claim 1 comprising the steps of:

a) Coating the substrate with the moisture-activated and tissue reactive adhesive on the at least one major surface thereof;

b) Applying a thermal energy to the first portion of said sealant patch to at least partially deactivate the adhesive on said first portion.

\* \* \* \* \*